United States Patent [19]

Hirschfeld

[11] Patent Number: 4,514,508

[45] Date of Patent: Apr. 30, 1985

[54] ASSAYING FOR A MULTIPLICITY OF ANTIGENS OR ANTIBODIES WITH A DETECTION COMPOUND

[75] Inventor: Steven Hirschfeld, New York, N.Y.

[73] Assignee: Biond Inc., New York, N.Y.

[21] Appl. No.: 395,263

[22] Filed: Jul. 6, 1982

[51] Int. Cl.$^3$ .................... G01N 33/54; G01N 33/58
[52] U.S. Cl. .................................. 436/518; 422/61; 435/7; 436/519; 436/531; 436/808; 436/809; 436/821
[58] Field of Search ............... 436/518, 809, 821, 519, 436/531, 808; 435/7; 422/61

[56] References Cited

U.S. PATENT DOCUMENTS

| | | | |
|---|---|---|---|
| 3,941,876 | 3/1976 | Marinkovich | 436/809 X |
| 4,016,043 | 4/1977 | Schuurs | 436/821 X |
| 4,138,213 | 2/1979 | Masson | 436/821 X |
| 4,283,383 | 8/1981 | Masson | 436/821 X |
| 4,307,190 | 12/1981 | Masson | 436/821 X |

OTHER PUBLICATIONS

Nydegger, U. E. et al., Jour. of Clin. Invest. 54, 297–309 (Aug. 1974).

Primary Examiner—Sidney Marantz

[57] ABSTRACT

Immunologic assay for biological and pharmaceutical substances sets forth a universal method for the qualitative and quantitative determination of biologic and pharmaceutical substances, thus eliminating the need for multiple samples at multiple laboratories and minimizing the time factor required for such determinations. The assay is based on the recognition and binding of an antibody and an antigen or hapten to form a complex, and the changes which occur in the antibody conformation and chemical properties when such a complex is formed.

A solid phase matrix, such as but not limited to a microtiter plate, is prepared having qualitative and/or quantitative spectrum of antibodies, or spectrum of antigens or haptens, bound in each position, which in the case of microtiter plates would be a sample well. The sample is then distributed to each of the positions or wells accordingly. If the sample contains an antigen or hapten that corresponds to the antibody in the well, or, if the sample contains an antibody that will bind the antigen or hapten in the well, an antigen-antibody complex will be formed. A detection compound is introduced and will recognize the formed complex and bind to the Fc portion of the antibody molecule. The detection compound is either labeled prior to the time of application or else is subsequently detected by radiolebeling, enzymatic or fluorescent reaction. Following serial washings, routine detection methods are employed.

19 Claims, No Drawings

ASSAYING FOR A MULTIPLICITY OF ANTIGENS OR ANTIBODIES WITH A DETECTION COMPOUND

BACKGROUND OF THE INVENTION

The detection of biological and pharmaceutical substances is a crucial aspect of research and clinical medicine. At present, each substance requires a separate assay, and these separate assays vary in their specificity and sensitivity. For some substances there is no currently available appropriate assay. Immunologic means are used to detect substances by those present assays which are among the most sensitive and specific. This technology is dependent upon the molecular interaction between an antibody, which is a protein that will specifically recognize and bind to a biological or pharmaceutical substance, which is known as the antigen or hapten. An antigen is a substance which is capable of producing an antibody. A hapten is a substance which alone is not capable of producing an antibody but when bound to a carrier which is an antigen is capable of producing an antibody directed against itself. Antibodies have particular regions or molecular domains, called binding domains, that are active in recognizing the antigen or hapten. It is not necessary to have the entire antibody molecule present, but only one of these binding domains in order to form a complex.

The degree of specificity in the recognition and binding of an antibody and an antigen or hapten is dependent upon the extent of uniqueness of the antigen's or hapten's 3-dimensional molecular structure and chemical properties and the extent of the correlation between those properties and the antibody's structure and properties. Two different antigens or haptens may have some aspect of their structure in common, and this can lead to the phenomenon of cross reactivity where the same antibody will recognize both antigens or haptens. To minimize this problem, it is important that the antibodies be as specific as possible. The recent development of hybridoma technology allows the selection for antibodies of high specificity. These antibodies have been employed in clinical assays for a few select antigens, with each test being for only one antigen. A particular research or clinical problem may indicate a need for testing for several antigens, thus requiring several separate assays.

The principle of such immunological assays is to detect the presence of a complex formed by the interaction of an antigen and an antibody. Current technology uses one of several methods to detect these complexes. One method employs a second antibody which is labeled either radioactively or enzymatically and which is directed against the same antigen. This will interact with the complex by binding to the antigen, sandwiching it between the two antibodies. These complexes are separated from unbound antigen or antibody by centrifugation if the assay is done in a liquid phase or serial washings if the assay is done on a solid phase. The presence of label is interpreted as a positive result and can be quantitated.

Another method uses highly purified antigen that is labeled and which competes with the test antigen for binding to the antibody in forming a complex. These complexes are separated from unbound antigen or antibody as described above. In this method the absence of label is interpreted as a positive result and can be quantitated. This method relies upon a constant supply of highly purified labeled antigen, as well as the highly specific antibody required by the first method.

A third approach, crossed immunoelectrophoresis (CIE), involves the formation of antigen-antibody complexes in a three dimensional matrix, with the visualization of these complexes using stains. This method requires substantially more antibody and antigen than the other methods and the utilization of special high voltage electrical equipment. It is therefore more expensive and cumbersome than other methods, but is able to resolve complex mixtures of antigens.

PRIOR ART STATEMENT

Currently, there is no method available which can analyze complex mixtures of antigens that is sensitive, portable, and economical.

U.S. Pat. No. 4,315,907 describes the simultaneous determination of different antibodies in a single serum sample by using solid phase binding agents for the respective ligands to be determined which are differentially separable from each other, thereby permitting the use of a single label rather than a different label for each ligand to be determined. This system has only been used to resolve two different antibodies using rabbit anti-human globulin and requires physical separation of the solid phases and separate detection assays. It requires a high degree of relatedness in the ligands to be detected with a possibility of quantitative error in the separation of the solid phases. In addition, it is limited by the number of solid phases which can be conveniently separated and, in the examples cited, consists of two.

The present invention is capable of resolving mixtures of ligands with at least a 10-fold greater degree of complexity and with greater precision since it does not require the manipulations associated with physical separation of solid phases and does not depend upon any relatedness among the ligands to be detected.

U.S. Pat. No. 4,307,190 describes the use of a component of mouse ascitic fluid termed euglobulin, and refers to British patent specification no. 1508133 regarding Clq, to detect antigen-antibody complexes by means of the agglutination of antigen-antibody coated latex beads. The method is based upon euglobulin's ability to bind to antigen-antibody complexes but not to free antibody or antigen and result in the aforementioned agglutination. This method is incapable of the simultaneous resolution and determination of a mixture of antigens or antibodies, but requires multiple serial determinations.

U.S. Pat. No. 4,308,026 describes a sensitive immunologic assay for low molecule weight haptens. It requires both purified antibody and purified hapten. It is incapable of resolving complex mixtures of haptens and in this way the present invention differs from it.

U.S. Pat. No. 4,294,817 is a surface immunoassay designed to resolve one component out of a mixture in two steps. The present invention differs in that it is possible to resolve more than one component from such a mixture.

U.S. Pat. No. 4,298,687 can detect one antigen at a time by use of a binding partner which is subsequently attached to a solid phase. The assay consists of determining the amount of unreacted binding partner. This method again is unable to resolve complex mixtures.

An advancement in the state of the art would arise from a technique which combined the portability, economy, sensitivity, and specificity of the prevalent techniques with the resolving capability of CIE. The feasibility of such a technique would be dependent upon a novel approach of detecing antigen-antibody complexes. The advantage of the present invention is the simultaneous resolution and determination of a mixture of antigens, haptens, or antibodies. The present invention, thus, provides such a desired approach.

SUMMARY OF THE INVENTION

This is a class of naturally occurring compounds having the characteristic of recognizing the conformational change in the Fc portion of an antibody, which change typically occurs when the antibody is bound to an antigen. The recognition is achieved by binding. The members of the class are known to those having ordinary skill in the art, and include complement, any of its components (such as Clq). For the purposes of this invention, the members of the class are referred to as "Detection Compounds.

The present invention discloses a use for such Detection Compounds such as complement or its components in detecting antigen-antibody complexes, where the detection method relies on changes that occur in antibody conformation and chemical properties when an antigen-antibody complex is formed. The use of such Detection Compounds allows detection of an antigen-antibody complex independent of the particular antigen or antibody. The invention thus discloses a universal means for detecting antigen-antibody complexes. These means can be applied to the quantitative and qualitative detection of such complexes in a variety of clinical and research settings. Methods for producing these compounds are described. Examples of applications are given.

DETAILED DESCRIPTION OF THE INVENTION

The present invention utilizes conventional techniques of biochemistry, cell culture, and immunology. For a review of these methods see *Methods In Enzymology*, Academic Press, New York, 1955-1981.

According to the present invention, a process is described which utilizes the recognition by a Detection Compound of antigen-antibody complexes. For the purposes of illustrating the laboratory technique for the application of the invention, the Detection Compound which will be described hereinafter is complement or its component Clq.

The series of serum proteins known as complement recognize antigen-antibody complexes by binding to what is termed the Fc portion of the antibody molecule (see Volanakis, J. E. and R. M. Stroud, *J. of Immunol. Methods*, Vol.2. p.25 (1972)). Specifically, what are termed the early components of complement, namely the protein known as Clq, will bind to an antibody molecule in the appropriate configuration (see Burton, D. R., et al., *Nature*, Vol.288, pp.338-344 (1980)). Clq has been purified (see Volanakis & Stroud, op. cit.) and labeled according to the methods of Heusser, C. et al. (*J. of Immunol.*, Vol.110, p.820 (1973)) and used to detect preexisting antigen-antibody complexes in human serum(Zubler, R. H., G. Lange, P. H. Lambert, & P. A. Miescher, *J. of Immunol., Vol.*116, pp.232-235 (1976); and Pohl, E., et al., *J. of Immunol. Methods*, Vol.40, p.313 (1981)). The present invention employs the principle of specific recognition of antigen-antibody complexes by complement, or components thereof, as applied to the formation of such complexes during the detection assay, in contrast to the detection of preexisting antigen-antibody complexes. In addition, the present invention is utilized to detect simultaneously multiple antigens and therefore has a higher degree of specificity than previous methods for the detection of single antigens.

The general principle of the assay for the detection of antigens or haptens on a solid phase matrix, such as but not limited to (hereinafter the phrase "such as" shall mean "such as but not limited to") a microtiter plate made of some appropriate material such as polyvinyl chloride, is as follows:

(1) Antibody directed against one or more specific antigens or haptens are prepared by an appropriate means. The antibodies may be of the class IgG or any other appropriate class, such as IgM, or they may be a portion of an antibody molecule with sufficient informatiion to specifically recognize an antigen or hapten and bind complement or any of its components.

(2) The antibody or antibodies or portions thereof are applied to the solid phase matrix. If multiple antibodies or portions thereof are utilized each different antibody is placed in a different position in the solid phase matrix.

(3) The solid phase is rinsed with an appropriate buffer to remove excess antibody.

(4) A non-specific coating compound, such as ovalbumin, serum albumin, or gelatin, is applied to the solid phase.

(5) The solid phase matrix is rinsed again to remove any excess coating compound.

(6) Test sample in solution is applied to the solid phase matrix and allowed to incubate.

(7) The solid phase matrix is rinsed against to remove any unbound test sample.

(8) A detection compound consisting of serum complement or any of its components is applied to the matrix at an appropriate dilution in an appropriate buffer.

(9) The solid phase matrix is rinsed thoroughly again to remove excess detection compound.

(10) The detection compound signal is detected by any appropriate direct or indirect means, such as using labeled antibody directed against complement or any of its components such as Clq, or using labeled complement or any of its components. Examples of labels are radioactive element, fluorescent dye, an enzyme, or opaque particles such as latex beads.

These general principles, stated above, of the assay are illustrated specifically in Examples 1, 2, and 3 below.

The general principle of the assay for the detection of antibodies, as contrasted with the detection of antigens or haptens, on a solid phase matrix, such as a microtiter plate made of polyvinyl chloride, is as follows:

(1) Antigens or haptens are prepared by any appropriate means and, if need be, linked to an appropriate carrier molecule, such as serum albumin.

(2) The antigens or haptens or antigen-or-hapten carrier complexes are applied to a solid phase matrix. If multiple antigens or haptens or antigen-or-hapten carrier complexes are utilized each different compound is placed in a different position in the solid phase matrix.

(3-10) General principles 3 through 10, stated above, apply here equally.

These general principles of the assay are illustrated specifically in Examples 4, 5, and 6 below.

The detection method described can be applied to any assay system utilizing immunologic techniques, such as solid or liquid phase radioimmunoassays, solid or liquid phase enzyme linked immunoadsorbent assays (ELISA), immunomicroscopy, immunoelectrophoresis, or immunodiffusion techniques.

For convenience in carrying out the assay, a test kit is provided. It includes (a) a solid phase matrix having either antigens or haptens, antibodies or portions thereof, or a combination of antigens, haptens, antibodies, and portions of antibodies attached in indentifiable positions of the solid phase matrix; and (b) the Detection Compound; and (c) labeled antibody or portions thereof directed against the Detection Compound.

The kit may optionally contain buffer, ovalbumin, and such other reagents as may be necessary to allow the chemical and biological reactions to take place, all of which are known to those of ordinary skill in the art.

The invention will now be described in more detail with reference to specific examples.

EXAMPLE NO. 1

Testing for a Single Antigen or Hapten on a Solid Phase Matrix (A) Preparation of Gammaglobulin. Gammaglobulin is prepared according to the method of Levy, H. B. and H. Sober, *P.S.E.B.M.*, Vol.103, p.250 (1960), by passing serum containing antibody directed against the antigen or hapten to be tested through a DEAE-cellulose column (Whatman DE52) equilibrated with 0.0175 sodium phosphate buffer pH 6.3 and eluted with the same buffer. The IgG is eluted at the void volume.

(B) Preparation of Ovalbumin. Commercially obtained ovalbumin is dissolved as a 1% solution in phosphate buffered saline ("PBS"), containing 0.9% sodium chloride, 0.02% potassium chloride, 0.115% dibasic sodium phosphate, and 0.02% monobasic sodium phosphate, pH 7.4 with 0.01% phenol red.

(C) Preparation of Microtiter Plates. The IgG prepared above is diluted 1:1,000 in PBS pH 7.4, and 25 microliters are carefully pipetted into the bottom of each of 96 wells in polyvinyl chloride plates (Cooke Laboratory Products, Cat. No. 1-220-24B). Plates are incubated at 25° C. for 30 minutes in a humidified chamber. The plates are washed two-to-four times with excess PBS and then the wells are filled with the ovalbumin solution and incubated at 25° C. for 30 minutes in a humidified chamber. They are washed two-to-four times with PBS and are now ready for either immediate application of the antigen or else may be stored covered at 4° C.

(D) Preparation of Complement. Lyophilized commercial complement is restored as per instructions or C1q is isolated from fresh serum by the method of Volanakis and Stroud (*J. of Immunol. Methods*, Vol.2, p.25 (1972)) and stored in aliquots as a 1% solution in buffered saline at minus 70° C.

(E) Application of Antigen to the Plates. Either 25 or 50 microliters of PBS is pipetted into each well on the plate except for the first and last columns. 50 or 100 microliters of test sample or mixture of antigens in solution are added to the first column of wells in the plate and serially diluted in PBS across the rows. The plates are incubated at 25° C. for 3 hours in a humidified chamber and then washed four-to-five times with buffered saline.

(F) Detection of Antigen-Antibody Complexes. Either C1q diluted 1:100 or restored complement diluted 1:10 are prepared, and 25 microliters are pipetted into each well. The plates are incubated for 30 minutes at 25° C. in a humidified chamber. They are washed 5 times with PBS.

(G) Preparation of Labeled Anti-C1q Gammaglobulin. IgG directed against complement component C1q is purified from rabbit serum as descirbed above for the purification of IgG. It is then either radioactively labeled with 125I by iodination (Hutchinson & Zigler, *Applied Microbio.*, December 1974, pp.935-942) to a specific activity of 1 mC/mg or labeled with peroxidase according to the method described by Nakane, P. K. & A. Kawaoi, *J. Histochem. Cytochem.*, Vol.22, pp.1084-1091 (1974) or with fluorescin (antibody against human C1q FITC, Calbiochem, Cat. 741901) or rhodamine.

(H) Detection of Antigen-Antibody C1q Complexes. 25 microliters of an appropriate dilution of labeled anti-C1q is added to each well and the plates are incubated at 25° C. for two hours in a humidified chamber. They are subsequently washed ten times with PBS and the signal is detected by appropriate means (e.g., the wells are separated from the plate and counted in a gamma counter or exposed to photographic film for radioactive label or exposed to light of the appropriate wavelength for the fluorescent dye or incubated with the peroxidase substrate 3-amino-9-ethyl carbazole for peroxidase label). The relative antigen level in each row is calculated as the ratio: strength of signal minus negative control divided by strength of positive control minus negative control for the 50% level of the positive control. This may be represented by the following formula:

$$\text{antigen level} = \frac{\text{test substance} - \text{negative control}}{\text{positive control} - \text{negative control}}$$

where negative control = background positve control = 50% of maximum signal.

EXAMPLE NO. 2

Alternative Technique for Testing for a Single Antigen or Hapten

This example illustrates the use of labeled C1q as the detection compound. The assay is performed using the methods described in Example 1, steps A through E, followed by:

(F) Preparation of Labeled C1q. Either 50 micrograms of C1q or 200 micrograms of serum complement are either radio labeled using lactoperoxidase according to the methods of Heusser, C., et al. (Heusser, C., M. Boesman, J. H. Nordin, and H. Isliker, *J. of Immunol.*, Vol. 110, p.820 (1973)) or labeled with peroxidase according to the method described by Nakane, P. K. et al. (Nakane, P. K. and A. Kawaoi, *J. of Histochem. Cytochem.*, Vol.22, p.1084-1091 (1974)).

(G) Detection of Antigen-Antibody Complexes. Either labeled C1q diluted to 1:100 or labeled complement diluted 1:10 are prepared, and 25 microliters are pipetted into each well. The plates are incubated for 30 minutes at 25° C. in a humidified chamber. They are then washed 10 times with PBS.

(H) Detection of Antigen-Antibody C1q Complexes. The plates in step G are then processed by appropriate means for signal detection (e.g., the wells are separated from the plate and counted as described in step H of Example 1). The relative antigen level in each row is calculated as in step H of Example 1.

In either Example 1 or 2 it is not necessary that the C1q and antibody be derived from the same species because there is cross species reactivity of C1q and IgG (Alexander, R. J., and R. R. Porter, *J. of Biochem.*, Vol.145, pp.177–183 (1975) and Hoffken, K., P. J. McLaughlin, M. R. Price, V. E. Preston, & R. W. Baldwin, *Immunochem.*, Vol.15, pp.409–412 (1978)).

EXAMPLE NO. 3

Testing for Multiple Antigens or Haptens in a Single Sample

This example illustrates the use of the principles of the methods described in Examples 1 and 2 to detect several types of antigens or haptens simultaneously on a signle plate and even the resolution and analysis of complex mixtures of antigens or haptens.

The assay is performed using the methods described in Example 1, steps A and B, followed by:

(C) Preparation of Microtiter Plates. Various IgG preparations directed against different antigens or haptens are each diluted to 1:1,000 in PBS pH 7.4, and 25 microliters are carefully pipetted into the bottom of each of 96 wells in polyvinyl chloride plates. Each row or column can receive a different IgG directed against a different antigen or hapten. Plates are incubated at 25° C. for 30 minutes in a humidified chamber. The plates are washed two-to-four times with excess PBS and then the wells are filled with the ovalbumin solution and incubated at 25° C. for 30 minutes in a humidified chamber. They are washed two-to-four times with PBS and are now ready for either immediate application of the antigen or else may be stored covered at 4° C.

(D and E) Steps D and E are the same as in Example 1.

(F, G, and H) Steps F,G, and H are the same as in either Example 1 or Example 2.

The applications for the methods described in Examples 1, 2, and 3 are numerous. They include, but are not limted to:

(1) The analysis of body fluids, such as whole blood, ascitic fluid, urine, semen, milk, glandular secretions, bone marrow aspirate, or suspensions of whole or broken cells, for the presence of pathogenic microbes.

(2) The detection and quantification of drugs, toxins, hormones, mediators of inflammation, autoantibodies, or antigens associated with neoplastic disorders in serum or other body fluids or tissue suspensions.

(3) The serial analysis of a complex mixture of natural, semi-synthetic, or synthetic antigens to determine the course or prognosis of a clinical condition.

(4) The analysis of serum or other bloody fluids to determine the suitability of a recipient for a transfusion or tissue donation.

The assay can also be performed in the obverse mode; that is, binding antigen to a support matrix and subsequently applying a sample to be tested for endogenous antibody levels. This is followed by the detection of antigen-antibody complexes by one of the above described methods.

EXAMPLE NO. 4

Testing for Immunoglobulins

This example illustrates the use of the principles of the assay to detect immunoglobulins.

(A) Preparation of Purified Antigen. An example of the use of the antisera to detect antibody against rubella will be illustrated. Commercial rubella antigen (Flow Laboratories Cat. No. 41-827-41) is suspended in PBS pH 7.4 at a dilution of 1:16.

(B) Preparation of Ovalbumin. Ovalbumin is dissolved as a 1% solution in PBS pH 7.4 with 0.01% phenol red.

(C) Preparation of Microtiter Plates. 25 microliters of the antigen prepared above are carefully pipetted into the bottom of each of 96 wells in polyvinyl chloride plates and incubated and washed as described in step C of Example 1.

(D) Preparation of Complement. Complement is prepared as described in step D of Example 1.

(E) Application of Test Material to the Plates. The test material is applied to the plates according to the procedures described in step E of Example 1, except that instead of applying the "test antigen", it is the test material (e.g., human serum) that is applied.

(F, G, and H) The same procedures as in steps F, G, and H of Example 1 are followed.

EXAMPLE NO. 5

Alternative Technique for Testing for Immunoglobulins

This example illustrates the use of labeled C1q as the detection compound to detect immunoglobulins.

(A, B, C, D, and E) The first five steps of this example follow the procedures used in steps A, B, C, D, and E of Example 3.

(F, G, and H) The last three steps of this example follow the procedures used in steps F, G, and H of Example 2.

EXAMPLE NO. 6

Testing for Multiple Antibodies in a Single Sample

This example illustrates the use of the principles of the assay to detect several types of immunoglobulins.

(A) Preparation of Purified Antigen. Several antigens, such as rubella antigen (Flow Laboratories, Cat. No. 41-827-41), influenze A/HK/868 HA antigen (Cat. No. 40-060-44, Flow Laboratories, Rockville, MD), human IgG (Cat. No. 401105, Calbiochem, La Jolla, CA.), are suspended each in PBS pH 7.4 at an appropriate dilution, such as 1:16, 1:16, and 1:100, respectively.

(B) The same procedures as in step B of Example 4 are followed.

(C) Preparation of Microtiter Plates. 25 microliters of each of the antigens or haptens are carefully pipetted into the bottom of each of 96 wells in polyvinyl chloride plates. Each row or column can receive a different antigen or hapten. The plates are incubated and washed as described in step C of Example 1.

(D, E, F, G, and H) Steps D, E, F, G, and H are the same as in either Example 4 or Example 5.

The applications for the methods described in Examples 4, 5, and 6 are numerous. They include, but are not limited to:

(1) The checking of antibody titers over time in individuals convalescing from an infection.

(2) The checking of antibody titers to determine the efficacy of an antigen administered to an individual for use as a vaccine.

(3) The determination of the types and levels of antibodies in an individual with an autoimmune disorder.

(4) The determination of the types and levels of antibodies in an individual who is immunocompromised.

I claim:

1. A method for assaying the presence or level of a multiplicity of antigens or haptens in a liquid complex mixture comprising the steps of:
   (a) adding the test sample containing the antigens or haptens to a solid phase matrix to form antigen-antibody complexes, said matrix having attached to it in identifiable positions antibodies or portions thereof, said antibodies or portions thereof directed against the antigens or haptens;
   (b) adding to the mixture formed in step (a) a known amount of labeled Detection Compound for antigen-antibody complexes; and
   (c) measuring the amount of labeled Detection Compound which remains bound to one or more of the identifiable positions of the solid phase matrix, and correlating that measurement with the presence or level of antigen or hapten in the identified positions.

2. The method of claim 1 wherein the labeling agent of the Detection Compound is radioactive element, fluorescent dye, an enzyme, or opaque particles.

3. The method of claim 1 wherein the Detection Compound is complement or the Clq component of complement.

4. A method for assaying the presence or level of a multiplicity of antibodies in a liquid complex mixture comprising the steps of:
   (a) adding the test sample containing the antibodies or portions thereof to a solid phase matrix to form antigen-antibody complexes, said matrix having attached to it in identifiable positions antigens or haptens to which said antibodies, or portions thereof, can bind;
   (b) adding to the mixture formed in step (a) a known amount of labeled Detection Compound for antigen-antibody complexes; and
   (c) measuring the amount of labeled Detection Compound which remains bound to one or more of the identifiable positions of the solid phase matrix, and correlating that measurement with the presence or level of antibody or portion thereof in the identified positions.

5. The method of claim 4 wherein the labeling agent of the Detection Compound is radioactive element, fluorescent dye, an enzyme, or opaque particles.

6. The method of claim 4 wherein the Detection Compound is complement or the Clq component of complement.

7. A method for assaying the presence or level of a multiplicity of antigens or haptens in a liquid complex mixture comprising the steps of:
   (a) adding the test sample containing the antigens or haptens to a solid phase matrix to form antigen-antibody complexes, said matrix having attached to it in identifiable positions antibodies or portions thereof, said antibodies or portions thereof directed against the antigens or haptens;
   (b) adding to the mixture formed in step (a) a known amount of Detection Compound for antigen-antibody complexes;
   (c) adding to the mixture formed in step (b) a labeled agent selected from the group consisting of a labeled antibody or portions thereof directed against the Detection Compound and a labeled component of complement which recognizes the Clq component of complement; and
   (d) measuring the amount of labeled agent which remains bound to one or more of the identifiable positions of the solid phase matrix, and correlating that measurement with the presence or level of antigen or hapten in the identified positions.

8. The method of claim 7 wherein the Detection Compound added in step (b) is the Clq component of complement and adding in step (c) a labeled component of complement which recognizes the Clq component of complement.

9. The method of claims 7 or 8 wherein the label of the labeled agent in step (c) is radioactive element, fluorescent dye, an enzyme, or opaque particles.

10. The method of claims 1 or 7 wherein the test sample is a fluid or suspension of human origin.

11. The method of claim 10 wherein the fluid or suspension of human origin is serum, whole blood, ascitic fluid, urine, semen, milk, glandular secretions, bone marrow aspirate, or suspensions of whole or broken cells.

12. A method for assaying the presence or level of a multiplicity of antibodies in a liquid complex mixture comprising the steps of:
   (a) adding the test sample containing the antibodies or portions thereof to a solid phase matrix to form antigen-antibody complexes, said matrix having attached to it in identifiable positions antigens or haptens to which said antibodies, or portions thereof, can bind;
   (b) adding to the mixture formed in step (a) a known amount of Detection Compound for antigen-antibody complexes;
   (c) adding to the mixture formed in step (b) a labeled agent selected from the group consisting of a labeled antibody or portions thereof directed against the Detection Compound and a labeled component of complement which recognizes the Clq component of complement; and
   (d) measuring the amount of labeled agent which remains bound to one or more of the identifiable positions of the solid phase matrix, and correlating that measurement with the presence or level of antibody or portion thereof in the identified positions.

13. The method of claim 12 wherein the Detection Compound added in step (b) is the Clq component of complement and adding in step (c) a labeled component of complement which recognizes the Clq component of complement.

14. The method of claims 12 or 13 wherein the label of the labeled agent in step (c) is radioactive element, fluorescent dye, an enzyme, or opaque particles.

15. The method of claim 4 or 12 wherein the test sample is a fluid or suspension of human origin.

16. The method of claim 15 wherein the fluid or suspension of human origin is serum, whole blood, ascitic fluid, urine, semen, milk, glandular secretions, bone marrow aspirate, or suspensions of whole or broken cells.

17. A diagnostic pack for the simultaneous detection and quantification of a multiplicity of antigens or haptens, antibodies or portions thereof, or a combination of antigens, haptens, antibodies, and portions of antibodies, comprising of:
   (a) a solid phase matix having either antigens or haptens, antibodies or portions thereof, or a combination of antigens, haptens, antibodies, and portions of antibodies attached in identifiable positions of the solid phase matrix; and
   (b) labeled Detection Compound.

18. A diagnostic pack for the simultaneous detection and quantification of a multiplicity of antigens or haptens, antibodies or portions thereof, or a combination of antigens, haptens, antibodies, and portions of antibodies, comprising of:
(a) a solid phase matrix having either antigens or haptens, antibodies or portions thereof, or a combination of antigens, haptens, antibodies, and portions of antibodies attached in identifiable positions of the solid phase matrix;
(b) Detection Compound; and
(c) a labeled agent selected from the group consisting of a labeled antibody or portions thereof directed against the Detection Compound and a labeled component of complement which recognizes the Clq component of complement.

19. The diagnostic pack described in claim 18 wherein the Detection Compound in (b) is the Clq component of complement and the labeled agent in (c) is a component of complement which recognizes the Clq component of complement.

* * * * *